United States Patent [19]

Brown

[11] Patent Number: 4,708,018
[45] Date of Patent: Nov. 24, 1987

[54] DRILLING MUD DENSITY PROBE

[75] Inventor: Gregory D. Brown, Norman, Okla.

[73] Assignee: Technical Oil Tools Corporation, Norman, Okla.

[21] Appl. No.: 919,010

[22] Filed: Oct. 15, 1986

[51] Int. Cl.$^4$ .............................................. G01N 9/28
[52] U.S. Cl. ..................................................... 73/439
[58] Field of Search .......................... 73/439, 438, 302

[56] References Cited

U.S. PATENT DOCUMENTS

| 3,587,316 | 6/1971 | Kapteyn | 73/302 |
| 3,613,456 | 10/1971 | Hopfe et al. | 73/439 |
| 4,476,722 | 10/1984 | Bentkowski | 73/434 |

*Primary Examiner*—John Chapman
*Attorney, Agent, or Firm*—Norvell & Associates

[57] ABSTRACT

A self-cleaning probe for a drilling fluid or drilling mud density-testing apparatus comprises an elongated tube through which pressured air is supplied to a nozzle disposed in the mud-immersed end of the tube. A cleaning plunger is normally disposed in an axially spaced, inoperative position relative to the nozzle and is reciprocated by an actuator mounted on the other end of the tube to pass through the nozzle and thereby remove any deposits of congealed mud from the nozzle bore. In a preferred embodiment, a small quantity of water is introduced in the upper end of the tube concurrently with the actuation of the cleaning plunger. This ensures that the congealed mud in the nozzle bore will be sufficiently hydrated to be easily removed by the cleaning plunger. Additionally, the cleaning plunger may be passed through an elastomeric wiping element which removes congealed mud from the plunger before it is again retracted to its inoperative position relative to the nozzle.

8 Claims, 3 Drawing Figures

DRILLING MUD DENSITY PROBE

BACKGROUND OF THE INVENTION

1. Field of the Invention

The invention relates to a probe utilized for determining the density of drilling muds employed in the well drilling industry.

2. History of the Prior Art

The utilization of air bubble probes for monitoring the density of fluids is a technique that has long been practiced. Two such probes are employed and are inserted in the fluid at two different depths so that a pressure opposing the flow of bubbles from each of the two probes is produced on the probes which is proportional to the density of the fluid. Air bubbles are then forced through the probes and out the bottom ends thereof at a constant rate, and the pressure required to produce such constant flow through each of the two tubes is measured. The differential in such pressures is multiplied by a scaling factor to yield the density of the fluid.

This technique is quite satisfactory for use with clean process fluids which do not collect or congeal around the passageway through which the air bubbles are emitted. A sufficient constriction of the air bubble passageway obviously results in a higher pressure being required to maintain the constant flow of bubbles required for the measuring technique. Thus, the increased pressure would result in an erroneous mud density determination.

By their very nature, drilling fluids or drilling mud differ significantly from clean processed fluids because the drilling fluids are intended to collect or congeal in small passageways, such as the passageways through which air bubbles are emitted in a differential pressure density-measuring device. A conventional drilling fluid or drilling mud contains fine particles of clay in suspension which enter and accumulate in crevices and pores in the well bore during circulation of the drilling fluids as part of a rotary drilling operation. The clay in suspension is intended to gel and eventually close the opening through the wall rocks in the well bore to seal the openings against movement of fluid either from or into the well bore.

Mud weight- or density-measuring devices using the technique of measuring the differential pressure between two vertically spaced points in a predetermined volume of fluid had been used in conjunction with drilling operations. One such device periodically collects a mud sample having a specified volume. After the weight of each constant volume sample is determined by the differential pressure method, the fluid sample is completely flushed out of the test container before a new, fresh sample is collected through the use of a vacuum. The flushing action permits the instrument to accurately handle foamy mud or mud containing lost circulation materials. This mud-weighing system involves the intermittent sampling and weighing of the drilling fluid, and mud does not stand stagnant in the weighing unit resulting in a false weight recording. See Rogers, *Composition and Properties of Oil Well Drilling Fluids;* Gulf Publishing Company, 1963, pp. 65–67.

Drilling fluids or drilling mud is circulated through the well bore during a rotary drilling operation. This drilling fluid is used to carry drill cuttings from the bottom of the well to the surface, to lubricate the rotating drill pipe, and to close the pores of formations yielding high-pressure gas or water. Drilling fluid is also used to seal permeable low-pressure formations, fissures, or crevices through which the drilling fluid might otherwise circulate.

Drilling fluid must also have a sufficient density to provide hydrostatic pressure to prevent high-pressure gas, oil, or water from entering the well in a sufficient quantity and rate to cause a blowout. If a high-pressure gas is encountered during drilling, the density of the "gas-cut" drilling fluid containing entrained gas bubbles is reduced, perhaps to such an extent as to permit a sudden flow of high-pressure gas to enter the well and violently eject the drilling fluid. The density of the drilling fluid is critical in maintaining an opposing hydrostatic pressure to prevent extraneous fluids or gases from entering the well. For example, drilling fluids weighing 5 to 18 pounds per gallon will ordinarily be sufficient to control formation fluids, but when high-fluid pressures are encountered, heavier drilling fluids must be employed. Hydrostatic pressures of about 0.7 psi per foot may become necessary to maintain adequate hydrostatic pressure.

The density of the drilling fluid can be significantly reduced when gas is occluded in the drilling fluid. When sufficient gas is entrained in the fluid to seriously reduce the density, the differential pressure between the formation and the well is increased and additional gas can enter the well. The volume of gas in the material will also expand at lower pressures contributing to a loss in drilling fluid density.

Drilling fluid or drilling mud comprises a special mixture of clay, water, and chemical additives, pumped downhole through the drill pipe and drill bit. The mud cools and lubricates the drill bit and drill pipe and carries rock cuttings to the surface. The mud serves as a plaster to prevent the wall of the borehole from crumbling or collapsing. Drilling mud also provides the weight or hydrostatic head to prevent extraneous fluids, such as natural gas, from entering the well bore to cause a potential blowout. Among the properties of clay-laden fluids that are important in determining their performance as circulating fluids or muds in rotary drilling are: density, viscosity, colloidity, sheer or gel strength, and sand and salt content. The density of a drilling fluid depends upon the amount and specific gravity of the suspended solids therein. Clay-laden fluids of density and viscosity suitable for rotary drilling purposes range in weight from 8.0 to 24.0 pounds per gallon and have equivalent specific gravities of 0.96 to 2.88. Drilling fluid or mud weight is measured by the pressure developed by the fluid in pounds per square inch per hundred feet of depth.

To effect mud density determination by air bubble probes, it is necessary that the mud be collected in a tank or pit to a depth sufficient to position the two probes at significantly different elevations. When utilizing high-density muds under high-temperature conditions, the mud is prone to congeal or cake to an extent that prevents the passage of a probe-cleaning plunger through the bore of the probe, thus further complicating the prior art mud density-measuring technique.

SUMMARY OF THE INVENTION

This invention provides a self-cleaning probe for determining the density of well drilling mud contained in a tank by the air bubble technique. The nozzle element of the probe which emits the air bubbles is mounted on the bottom end of an elongated tube having a substantially greater diameter adjacent the nozzle than the axial passage defined by the nozzle through which the air bubbles are released into the surrounding drilling mud. A cleaning plunger is positioned on the end of the rod which traverses the length of the probe tube and is connected at the upper end of the probe tube to an actuator, such as a pneumatic cylinder or electrical solenoid. The cleaning plunger is just slightly smaller in diameter than the axial passageway defined by the nozzle and, hence, when the cleaning plunger is disposed in its inactive position within the large-diameter bore of the probe tube, it offers no impediment to the flow of air through the probe tube. Periodically, the actuating mechanism is energized to effect a reciprocation of the cleaning plunger through the axial passageway of the nozzle, thus effecting a cleaning of the nozzle and removal of any mud that has congealed on the surfaces of the axial passageway.

In a preferred modification of this invention, a small quantity of water is injected around the plunger and into the mud. If such mud is caked or congealed around the bottom of the nozzle, the small quantity of water hydrates such mud and softens it, and thus permits the ready passage of the cleaning plunger through the nozzle bore and into the softened mud, thus assuring that the entire nozzle bore is cleaned of mud deposits. Also the water permits the retraction of the cleaning plunger to its inactive position, essentially free of any congealed mud.

If caking or congealing of the mud is not a problem, a further modification of this invention provides a cleaning apparatus for the cleaning plunger. After the cleaning plunger passes out of the nozzle, it enters into the constricted bore of an elastomeric wiping element which effects a wiping away of any mud adhering to the probe, so that when the plunger is withdrawn back through the nozzle and restored to its inoperative position within the probe tube, it is essentially clean and free of any congealed mud.

This self-cleaning operation of the improved probe may be controlled in accordance with the pneumatic or electrical system that monitors the drilling mud density and the depth of the drilling mud in the tank, hence the probe-cleaning operation can be accomplished automatically, at any desired intervals, without requiring operator time or attention, or interrupting the monitoring process for more than a few seconds.

Further advantages of the invention will be readily apparent to those skilled in the art from the following detailed description, taken in conjunction with the annexed sheets of drawings, on which is shown a preferred embodiment of the invention.

DESCRIPTION OF PREFERRED EMBODIMENTS

Figure 1:
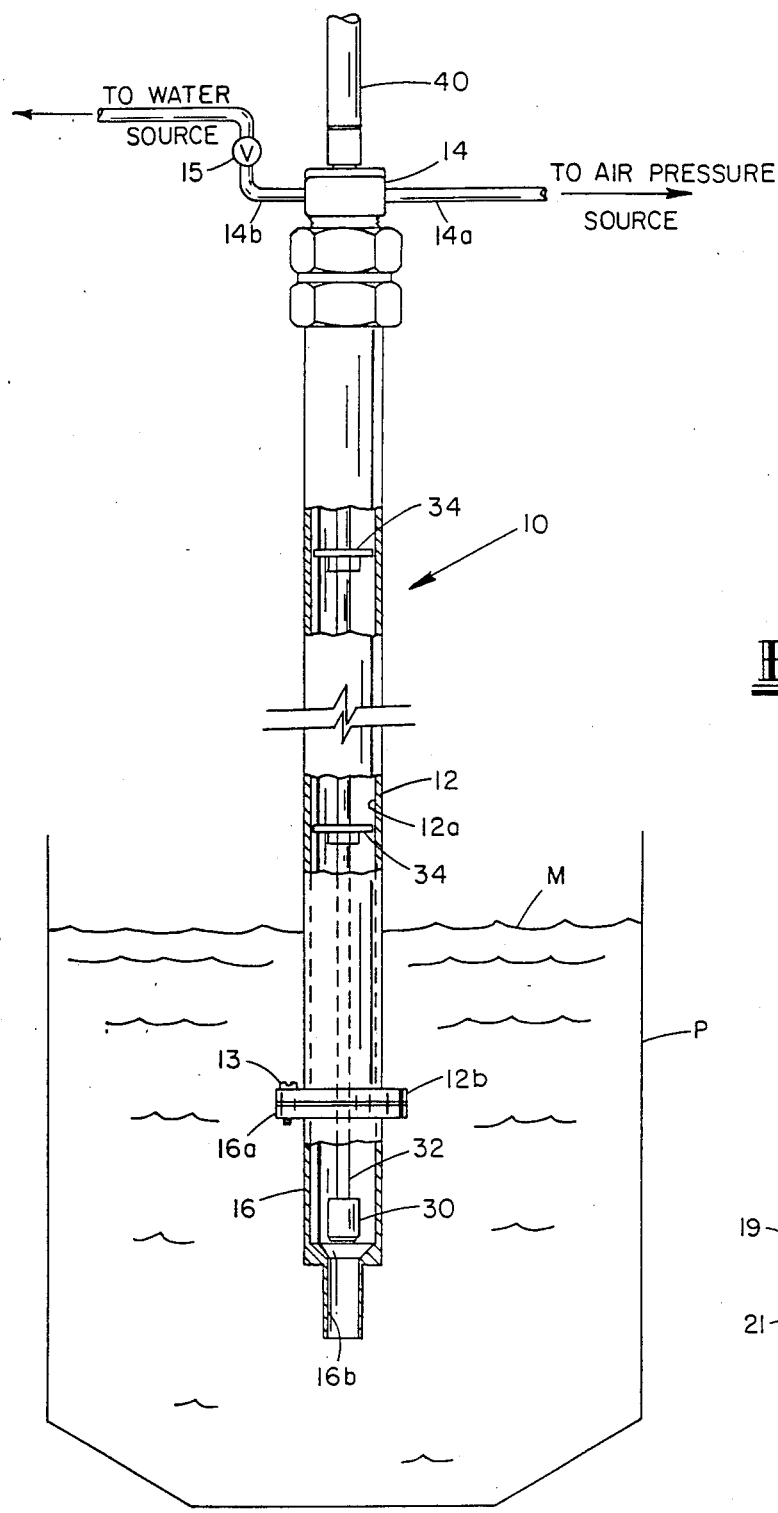
FIG. 1 is a schematic elevational view, partly in section, of a drilling mud density probe embodying this invention, with the cleaning plunger shown in its inoperative position.

Referring to the drawings, a self-cleaning mud density probe 10 is shown in operative relationship with respect to a body of drilling mud M contained within a suitable tank or pit P. Probe 10 comprises an elongated tubular body portion 12 having a manifold 14 conventionally secured to its upper end, and providing a first connection 14a between the bore 12a of the body portion 12 and a variable pressure source of air, and a second connection 14b to a water source through a control valve 15. Valve 15 may be electrically or fluid pressure actuated. The bottom end of the tubular body portion 12 is attached by a flange 12b and bolts 13 to a corresponding flange 16a formed on the upper end of a nozzle-defining member 16. The lower end of member 16 defines a constricted diameter nozzle 16b for emitting air bubbles therethrough at a controlled volumetric flow rate. The diameter of nozzle 16b is substantially less than the diameter of that portion of bore 12a which is adjacent the nozzle member 16.

A cleaning plunger 30 is suspended within the elongated tubular body portion 12 by a rod 32 which is suitably supported by the manifold structure 14 at the top of the tube 20. A plurality of spacer rings 34 are secured in spaced relationship along the rod 32 to keep the rod 32 centered with respect to the bore 12a of the tubular body 12. Plunger 30 has a diameter just slightly less than the bore of the nozzle portion 16b so that when the plunger 30 is traversed through the nozzle 16b, a wiping and cleaning of such bore will occur. Plunger 30 in its inactive postion shown in FIG. 1 will not impair the flow of air through the probe. Obviously, tubular body portion 12 could have a reduced diameter above this position of plunger 30.

Figure 2:
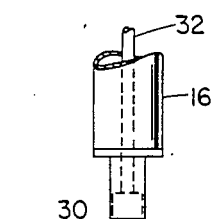
FIG. 2 is a view of the bottom portions of the cleaning probe of FIG. 1, showing the probe in its fully advanced cleaning position subsequent to traversing the nozzle passageway.

The top end of support rod 32 is secured to the actuating element (not shown) of a linear actuator 40 mounted on manifold 14. Actuator 40 may comprise either an electric solenoid or a fluid pressure actuator. In either event, actuator 40 is capable of advancing plunger 30 from its inoperative position shown in FIG. 1 to its advanced cleaning position shown in FIG. 2 wherein the plunger 30 has traversed the nozzle bore 16b. For this purpose, the leading edge of the plunger 30 is tapered to facilitate the ready passage of the plunger into the nozzle bore.

The aforedescribed apparatus is positioned at a desired depth within the mud pit P and is employed in conjunction with an identical mud density probe located at a different depth in the same mud. Air is then bubbled through the nozzle 16b at a constant rate determined by adjustment of conventional regulators (not shown). When a constant rate of flow is established in each nozzle 16b, the difference in pressures between the nozzles is directly proportional to the density of the mud, and may be multiplied by an appropriate scaling factor to yield the mud density in conventional fashion. Such operation of the probes is conventional.

Generally the mud density probes are continuously operated within the body of drilling mud M to provide continuous readings of the density of the drilling mud so that the drilling rig operator can make appropriate adjustments to the drilling mud to maintain the desired density. As a result, the drilling mud tends to congeal and collect in the nozzle portion 16b of the nozzle-defining member 16. Such collection of hardened drilling mud deposits obviously constricts the discharge area of the nozzle bore 16b and, hence, requires a higher pressure to maintain the desired constant rate of air flow. As a result, erroneous density readings will be produced if the congealed mud is permitted to remain in the nozzle bore 16b.

In accordance with this invention, the actuator 40 is periodically energized to drive the cleaning plunger 30 downwardly through the nozzle bore 16b to effect a removal of any congealed mud deposited thereon. This assures that the density readings will remain accurate. Additionally, if the mud around the nozzle 16b is caked or congealed, water valve 15 is momentarily opened, allowing a small quantity of water to pass through manifold 14 into the probe bore 12a and flow through the nozzle bore 16b to aid in hydrating and removing congealed mud from the path of plunger 30. The plunger 30 is then retracted by de-energizing the actuator 40 and the mud probe is restored to its normal operating condition without having to be removed from the mud pit. By utilizing fluid pressure control circuitry of the type described in co-pending U.S. patent application, Ser. No. 870,343 filed concurrently herewith, the cleaning of the nozzle portions of the mud density probes may be automatically accomplished at periodic intervals; hence, the possibility of error in the mud density readings produced by such probes is substantially eliminated.

Figure 3:
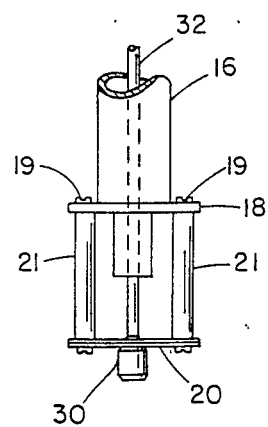
FIG. 3 is a schematic elevational view of a modification of this invention incorporating a plunger cleaning apparatus.

In accordance with a modification of this invention shown in FIG. 3, an annular mounting plate 18 is integrally formed or suitably secured to the lower portion of the nozzle-defining element 16 and provides a mounting for a plurality of elastomeric wiper rings 20 which are secured to the mounting plate 18 by bolts 19 and spacer tubes 21. The wiper rings 20 may be defined as an annular member having an internal bore which is of less diameter than the bore of the nozzle portion 16b and may be provided with a plurality of radially extending slits (not shown) to permit the wiping passage of an object therethrough. The stroke of the actuator 40 and cleaning plunger 30 is increased, so that plunger 30 passes through the wiper rings 20 to be cleaned thereby.

Although the invention has been described in terms of specified embodiments which are set forth in detail, it should be understood that this is by illustration only and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A mud density probe for determining the density of well drilling mud confined in a tank comprising: an elongated tube vertically insertable in the mud; manifold means secured to the upper end of said tube for connecting the bore of said tube to a variable pressure source of pressured air; nozzle means secured to the bottom end of said tube defining an axial discharge passage for bubbles of pressured air; said axial discharge passage having a bore of substantially smaller diameter than the bore of said tube adjacent said nozzle means; a cleaning plunger mounted in said tube bore for reciprocal movement, said plunger having an external diameter slightly less than said axial discharge passage, whereby passage of said plunger through said axial passage removes congealed mud from the surface of said axial passage and means for reciprocating said plunger through said axial passage to clean same.

2. The apparatus of claim 1 wherein said means for reciprocating said plunger comprises a reciprocable actuator mounted on the top of said tube, and means for connecting said plunger and said actuator.

3. The apparatus of claim 2 wherein said means for reciprocating said plunger comprises a reciprocable actuator mounted on the top of said tube, and a rod connecting said plunger and said actuator.

4. The apparatus of claim 1 further comprising means disposed below said nozzle means for wiping the peripheral surface of said plunger.

5. The apparatus of claim 4 wherein said means for wiping said plunger comprises an annular elastomeric element having a bore traversable by said plunger in wiping relationship.

6. A mud density probe for determining the density of well drilling mud confined in a tank comprising: an elongated tube vertically insertable in the mud; manifold means secured to the upper end of said tube for connecting the bore of said tube to a variable pressure source of pressured air; nozzle means secured to the bottom end of said tube defining an axial discharge passage for bubbles of pressured air; said axial discharge passage having a bore of substantially smaller diameter than the bore of said tube adjacent said nozzle means; a cleaning plunger mounted in said tube bore for reciprocal movement, said plunger having an external diameter slightly less than said axial discharge passage, whereby passage of said plunger through said axial passage removes congealed mud from the surface of said axial passage; means for reciprocating said plunger through said axial passage to clean same, and means for injecting water into said discharge passage to facilitate removal of congealed mud from said discharge passage.

7. The apparatus of claim 6 wherein said means for reciprocating said plunger comprises a reciprocable actuator mounted on the top of said tube, and means for connecting said plunger and said actuator.

8. The apparatus of claim 6 wherein said means for reciprocating said plunger comprises a reciprocable actuator mounted on the top of said tube, and said water-injecting means comprises a valve opened concurrently with the activation of said actuator.

* * * * *